United States Patent

Okawa

Patent Number: 6,063,887
Date of Patent: May 16, 2000

[54] 1-ACYLOXY-ORGANOTETRASILOXANE AND PRODUCTION METHOD FOR THE PREPARATION OF THE SAME

[75] Inventor: Tadashi Okawa, Chiba Prefecture, Japan

[73] Assignee: Dow Corning Toray Silicone Co., Ltd., Tokyo, Japan

[*] Notice: This patent is subject to a terminal disclaimer.

[21] Appl. No.: 08/985,539

[22] Filed: May 18, 1998

[30] Foreign Application Priority Data

Dec. 4, 1996 [JP] Japan .................................. 8-338866

[51] Int. Cl.$^7$ .................................................. C08G 77/08
[52] U.S. Cl. ............................... 528/23; 528/12; 528/14; 528/16; 528/15; 528/18; 528/19; 528/21; 528/34; 528/37; 528/41; 556/440; 556/442; 556/41
[58] Field of Search .................................... 556/440, 442, 556/470; 528/34, 37, 41, 12, 14, 15, 16, 18, 19, 21, 23

[56] References Cited

U.S. PATENT DOCUMENTS

| | | | |
|---|---|---|---|
| 5,095,085 | 3/1992 | Hara et al. | 528/41 |
| 5,268,396 | 12/1993 | Lai | 528/41 |
| 5,856,545 | 1/1999 | Okawa | 556/440 |

FOREIGN PATENT DOCUMENTS

43-9080  2/1991  Japan .

OTHER PUBLICATIONS

"Cationic Telomerization of Hexamethylcyclotrisiloxane . . . ", European Polymer Journal, vol. 17, 1981. pp. 413–419.

*Primary Examiner*—Melvyn I. Marquis
*Attorney, Agent, or Firm*—Larry A. Milco

[57] ABSTRACT

A 1-acyloxy-organotetrasiloxane represented by the general formula:

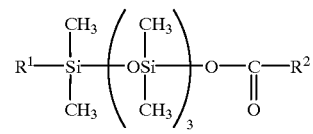

wherein $R^1$ is a monovalent organic group containing an acryloyloxy group or a monovalent organic group containing a methacryloyloxy group, and $R^2$ is a monovalent hydrocarbon group, and a process for producing the above mentioned 1-acyloxy-organotetrasiloxane, which is characterized by subjecting hexamethylcyclotrisiloxane to a ring-opening reaction with an acyloxysilane represented by the general formula:

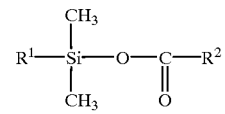

wherein $R^1$ is a monovalent organic group containing an acryloyloxy group or a monovalent organic group containing a methacryloyloxy group, and $R^2$ is a monovalent hydrocarbon group, in the presence of an acidic catalyst.

29 Claims, 2 Drawing Sheets

1-ACYLOXY-ORGANOTETRASILOXANE AND PRODUCTION METHOD FOR THE PREPARATION OF THE SAME

FIELD OF THE INVENTION

The present invention relates to a novel 1-acyloxy-organotetrasiloxane and a process for efficiently producing the siloxane.

BACKGROUND OF THE INVENTION 1-acetoxy-7-vinyl-octamethyltetrasiloxane (see Japanese Kokoku Patent No. Sho 43[1968]-9080) and 1-acetoxy-nonamethyltetrasiloxane (see European Polymer Journal Vol. 17, 413–419, 1981) have been known as 1-acyloxy-organotetrasiloxanes.

However, 1-acyloxy-organotetrasiloxanes having a monovalent organic group containing an acryloyloxy group or a monovalent organic group containing a methacryloyloxy group bonded to a silicon atom at one end of the molecular chain and an acyloxy group bonded to a silicon atom at the other end of the molecular chain have been unknown.

SUMMARY OF THE INVENTION

The 1-acyloxy-organotetrasiloxane of the present invention is represented by the following general formula (3):

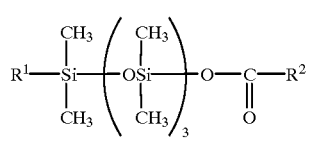

(3)

wherein $R^1$ is a monovalent organic group containing an acryloyloxy group or a monovalent organic group containing a methacryloyloxy group, and $R^2$ is a monovalent hydrocarbon group.

The process for the production of the 1-acyloxy-organotetrasiloxane of the present invention is also characterized by subjecting hexamethylcyclotrisiloxane to a ring-opening reaction with an acyloxysilane represented by the general formula (4):

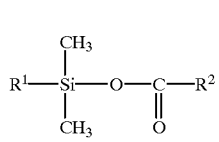

(4)

wherein $R^1$ is a monovalent organic group containing an acryloyloxy group or a monovalent organic group containing a methacryloyloxy group, and $R^2$ is a monovalent hydrocarbon group, in the presence of an acidic catalyst.

The object of the present invention is to offer a novel 1-acyloxy-organotetrasiloxane having a monovalent organic group containing an acryloyloxy group or a monovalent organic group containing a methacryloyloxy group bonded to a silicon atom at the end of the molecular chain and an acyloxy group bonded to a silicon atom at the other end of the molecular chain, and a process for efficiently producing such siloxane.

DETAILED DESCRIPTION OF THE INVENTION

Figure 1:
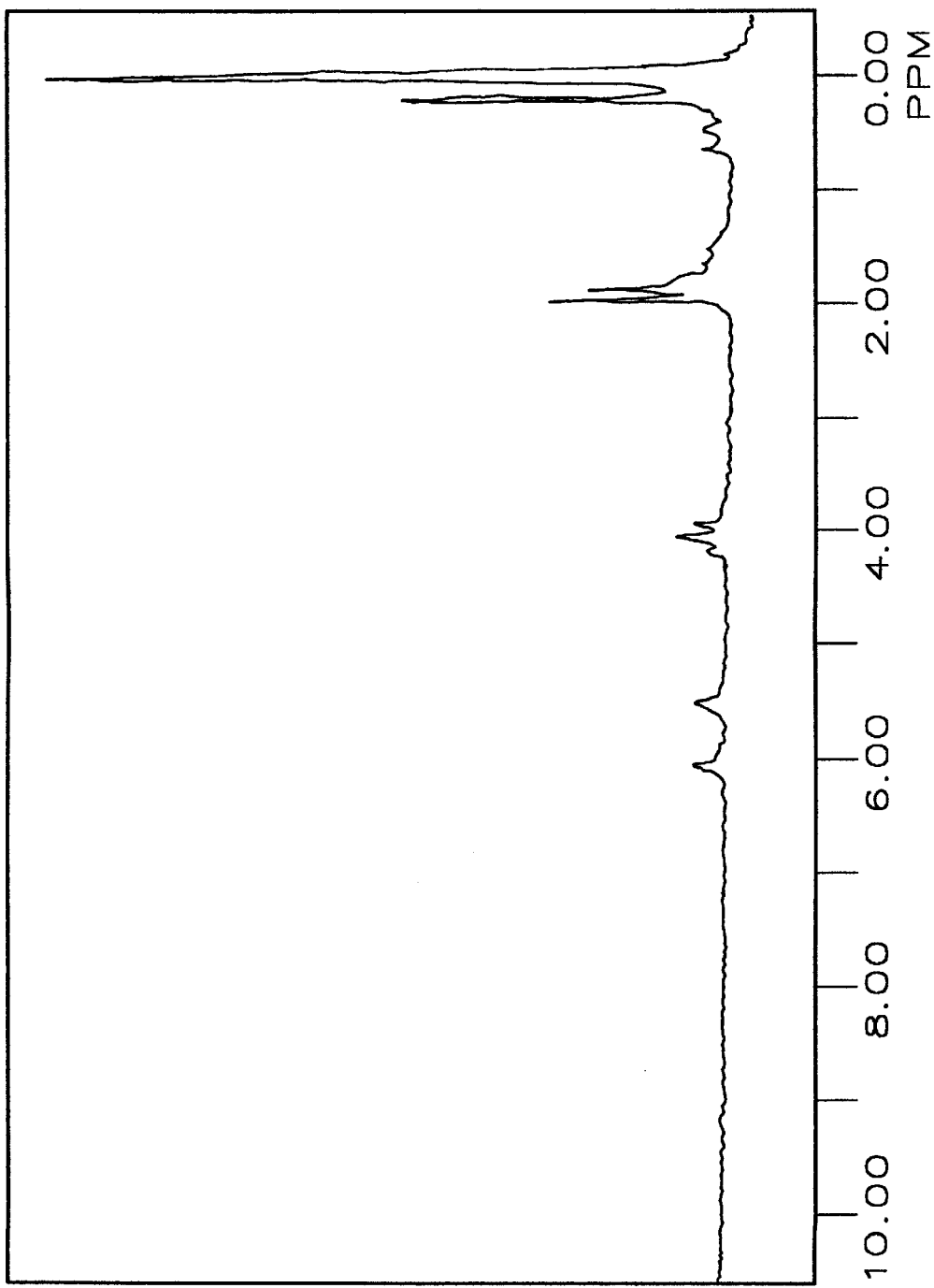
FIG. 1 is a chart of $^1$H-nuclear magnetic resonance analysis of the 1-acetyloxy-7-(3-methacryloyloxypropyl)-1,1,3,3,5,5,7,7-octamethyltetrasiloxane prepared in Example 1.
Figure 2:
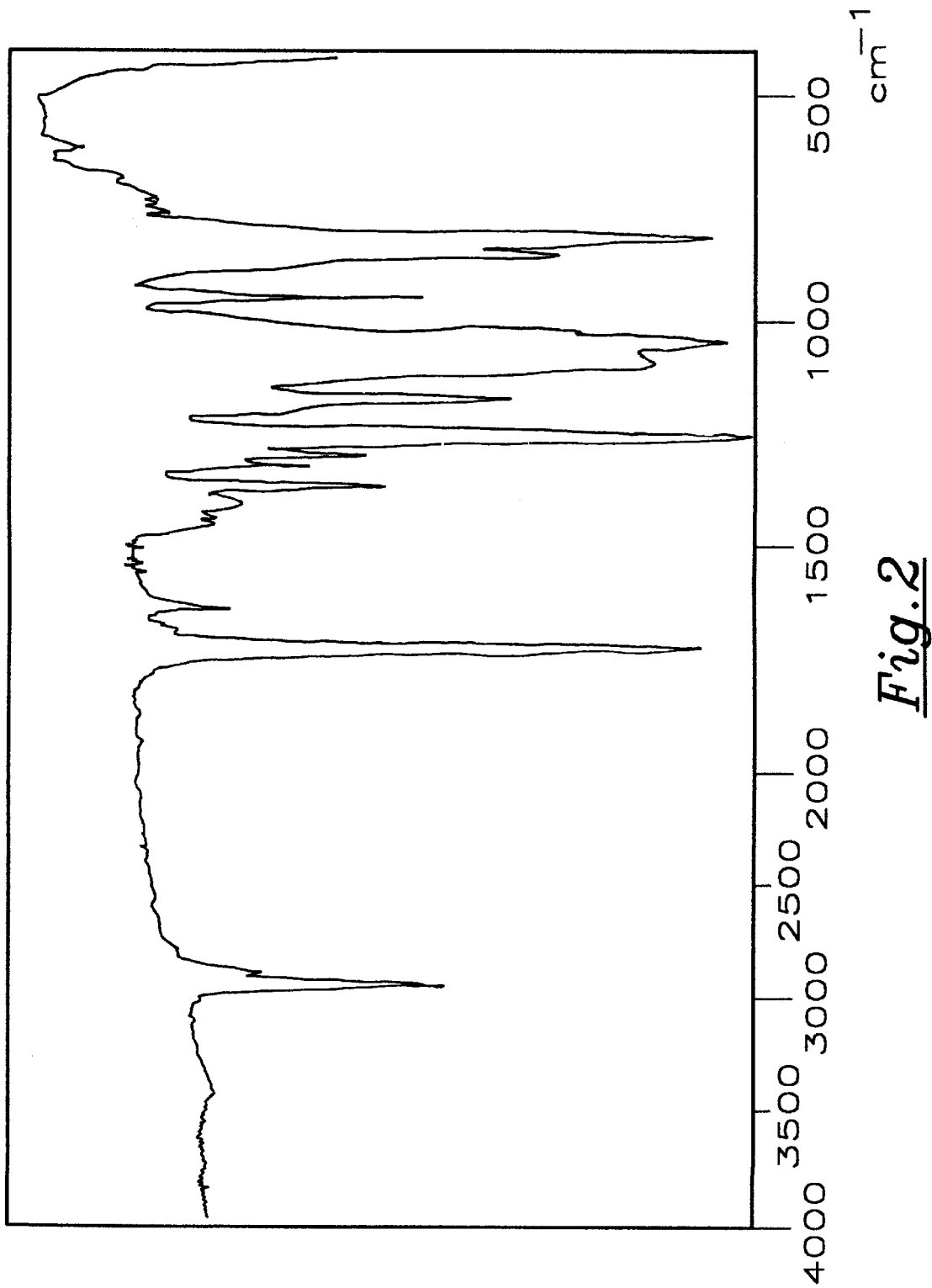
FIG. 2 is a chart of infrared spectroscopic analysis of the 1-acetyloxy-7-(3-methacryloyloxypropyl)-1,1,3,3,5,5,7,7-octamethyltetrasiloxane prepared in Example 1.

First of all, detailed explanations will be provided regarding the 1-acyloxy-organotetrasiloxane of the present invention.

The 1-acyloxy-organotetrasiloxane of the present invention is represented by the general formula (3) above. $R^1$ in this formula is a monovalent organic group containing an acryloyloxy group or a monovalent organic group containing a methacryloyloxy group. It is specifically exemplified by 3-acryloxypropyl, 6-acryloyloxyhexyl, and other acryloyloxyalkyl groups; 3-(2-acryloyloxyethyl-oxy)propyl and other acryloyloxyalkyloxyalkyl groups; 3-methacryloyloxypropyl, 6-methacryloyloxyhexyl, and other methacryloyloxyalkyl groups; 3-(2-methacryloyloxyethyl-oxy)propyl and other methacryloyloxyalkyloxyalkyl groups; preferably, it is an acryloyloxyalkyl group or a methacryloyloxyalkyl group, with methacryloyloxyalkyl being preferable from the standpoint of ease of manufacture and economic efficiency, and 3-methacryloyloxypropyl being especially preferable. Also, $R^2$ in the formula above is a monovalent hydrocarbon group specifically exemplified by methyl, ethyl, propyl, butyl, pentyl, and other alkyl groups; vinyl, allyl, butenyl, pentenyl, and other alkenyl groups; phenyl, tolyl, xylyl, and other aryl groups; benzyl, phenetyl, and other aralkyl groups, and, preferably, methyl.

Because the 1-acyloxy-organotetrasiloxane of the present invention has a monovalent organic group containing an acryloyloxy group or a monovalent organic group containing a methacryloyloxy group bonded to a silicon atom at one end of the molecular chain and an acyloxy group bonded to a silicon atom at the other end of the molecular chain, it allows for obtaining curable copolymers having hydrolytic silicon-bonded acyloxy groups by copolymerizing it with acrylic ester, methacrylic ester, styrene and other polymerizable vinyl monomers.

Next, detailed explanations will be provided regarding the process for the production of the 1-acyloxy-organotetrasiloxane of the present invention.

The production process of the present invention is characterized by subjecting hexamethylcyclotrisiloxane to a ring-opening reaction with an acyloxysilane represented by the above mentioned general formula (4) in the presence of an acidic catalyst. The acidic catalyst is exemplified by protonic acid catalysts and Lewis acid catalysts, with protonic acid catalysts specifically exemplified by hydrochloric acid, nitric acid, sulfuric acid, trifluoromethanesulfonic acid, trifluoracetic acid, with trifluoromethanesulfonic acid being especially preferable, and Lewis acid catalysts specifically exemplified by metal halides, such as $ZnCl_2$, $BeCl_2$, $TeCl_4$, $SnCl_4$, $FeCl_3$, $FeCl_2$, $SbCl_5$, $AlCl_3$, and the like. Because they suppress equilibration reactions due to siloxane bond rearrangement, selectively bring about the ring-opening reaction of the target hexamethylcyclotrisiloxane, and can suppress undesirable side reactions, metal halides exhibiting Lewis acid properties are preferable, with $ZnCl_2$ being especially preferable. Also, the activity of the catalyst in the ring-opening reaction can be conspicuously increased by using acid halides or acid anhydrides along with the metal halides exhibiting Lewis acid properties. Catalysts consisting of such metal halides exhibiting Lewis acid properties and acid halides or acid anhydrides are known as Friedel-Crafts acylation reaction catalysts. Such catalysts consist of a metal halide exhibiting Lewis acid properties and an acid halide or an acid anhydride. Although their mole ratio is arbitrary, 1 mole of acid halide and 0.5 mole of acid anhydride per 1 mole of metal halide are preferable stoichiometrically. In practice, however, it is preferable to use them in equivalent or greater amounts. Also, it is preferable that the acyl groups in the acid halides or acid anhydrides used in the catalysts should be the same as the acyl groups represented by the general formula (5):

(5)

in the acyloxysilane represented by the general formula (4) indicated above.

When hexamethylcyclotrisiloxane is subjected to a ring-opening reaction with an acyloxysilane represented by the above mentioned general formula (4) in the presence of an acidic catalysts, it is preferable to use acyloxysilane in an equimolar or greater amount relative to hexamethylcyclotrisiloxane. It is especially preferable to use a molar amount that is 1~1.5 times greater. Using organic solvents in the ring-opening reaction is optional, with the organic solvents exemplified by toluene, xylene and other aromatic solvents; hexane, heptane, and other aliphatic solvents. When only protonic acids or metal halides are used as the acidic catalysts, acyloxysilane, hexamethylcyclotrisiloxane, protonic acid or metal halide, and, as the occasion demands, an organic solvent, are mixed and reacted at room temperature or under heating. Also, when Friedel-Crafts acylation reaction catalysts consisting of a metal halide and an acid halide or an acid anhydride are used as the acidic catalysts, acyloxysilane, hexamethylcyclotrisiloxane, metal halide, acid halide or acid anhydride, and, as the occasion demands, an organic solvent, are mixed and reacted at room temperature or under heating. Otherwise, a metal halide can be mixed with an acid halide or an acid anhydride and heated to prepare a Friedel-Crafts acylation reaction catalyst in advance, whereupon acyloxysilane, hexamethylcyclotrisiloxane, and, as the occasion demands, an organic solvent, can be mixed and reacted therewith at room temperature or under heating. This is particularly preferable, because heating is necessary for the preparation of the Friedel-Crafts acylation reaction catalyst, and, if it is prepared in advance, the ring-opening reaction of hexamethylcyclotrisiloxane can be conducted at a low temperature.

Next, the ring-opening reaction is terminated, which is achieved by neutralizing the acidic catalyst with triethylamine, diethylamine, hexamethyldisilazane, and the like. The salts produced during this neutralization reaction can be removed by filtration or decantation. Then the 1-acyloxy-organotetrasiloxane of the present invention can be obtained by fractionating the reaction mixture. When such fractionation is conducted, it is preferable to use copper oxide, copper hydroxide, copper chloride, and other metal halides, oxygen, quinone compounds, amine compounds, hindered phenol compounds, phenothiazine, hindered phenols having an onium salt structure, and other polymerization inhibitors in order to prevent the reaction mixture from gelling.

EXAMPLES

The 1-acyloxy-organotetrasiloxane and process for the production of the same of the present invention will be now explained by referring to application examples.

Example 1

25.8 g (314.3 μmoL) sodium acetate and 30 g toluene were placed in a four-neck flask furnished with an agitator and the system was subjected to azeotropic dehydration by heating it for 30 minutes at the reflux temperature of toluene. After that, the system was cooled to 75° C. and 63 g (285.7 μmoL) 3-methacryloyloxypropyl dimethylchlorosilane was added dropwise. When the dropwise addition was over, the system was heated for 30 minutes at 80° C. under agitation. When a portion of the reaction mixture was analyzed using gas chromatography ("GLC" below), the peak of 3-methacryloyloxypropyl dimethylchlorosilane had disappeared. After that, a toluene solution was obtained by filtering off the by-produced sodium chloride and unreacted sodium acetate. After removing toluene from a portion of this toluene solution, analysis using GLC, infrared spectroscopic analysis ("IR" below), $^1$H-nuclear magnetic resonance analysis ("$^1$H-NMR" below) and gas chromatography-mass spectrometry ("GC-MS" below) showed that it consisted of 3-methacryloyloxypropyl dimethylacetyloxysilane represented by the following formula (6):

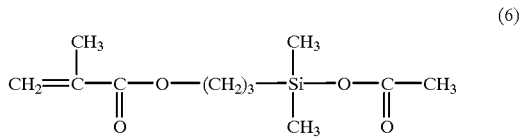

(6)

Next, when 7.6 g (56.5 μmoL) acetic anhydride and 3.5 g (25.7 μmoL) ZnCl$_2$ were placed in a separate four-neck flask furnished with an agitator and subjected to heating under agitation for 10 minutes at 70° C., ZnCl$_2$ was completely dissolved, and a dark red solution was obtained. After cooling it to room temperature, the entire amount of the previously prepared 3-methacryloyloxypropyl dimethylacetyloxysilane, 63.4 g (285.7 μmoL) hexamethylcyclotrisiloxane, and 0.003 g 2,6-di-t-butyl-4-methylphenol were placed in the flask, and the mixture was heated at 50° C. under agitation for 3 hours 45 minutes. When a portion of the reaction mixture was analyzed using GLC, it was found that 3-methacryloyloxypropyldimethylacetyloxysilane had been converted to 1-acetyloxy-7-(3-methacryloyloxypropyl)-1,1,3,3,5,5,7,7-octamethyltetrasiloxane represented by the following formula (7):

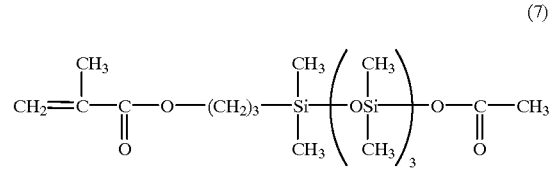

(7)

The ratio (reaction ratio) was 86%. After that, the system was neutralized by adding 2.9 g (28.3 μmoL) triethylamine. A toluene solution was obtained by removing the by-produced salt by decantation. 122.9 g of a liquid was obtained from this toluene solution by heating the low boiling point fraction at 80° C. under a reduced pressure of 1 mmHg for 30 minutes. Upon adding 0.09 g 3,5-di-t-butyl-4-hydroxyphenylmethyldimethylammonium chloride, 0.006 g hydroquinone monomethyl ether, and 0.006 g 2,6-di-t-butyl-4-methylphenol to 60 g of the liquid, 27.2 g of the 136~142° C./1 mmHg fraction was obtained (corresponds to a yield of 42%) by distillation under reduced pressure. Analysis of the fraction using ¹H-NMR and IR showed that it consisted of 1-acetyloxy-7-(3-methacryloyloxypropyl)-1,1,3,3,5,5,7,7-octamethyltetrasiloxane represented by the following formula (8):

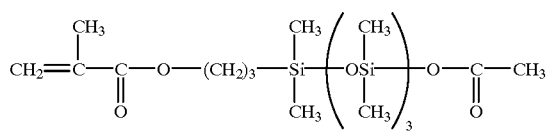

(8)

The purity of the siloxane as determined by GLC was 90.7%.

Example 2

25.8 g (314.3 μmoL) sodium acetate and 30 g toluene were placed in a four-neck flask furnished with an agitator and the system was subjected to azeotropic dehydration by heating it for 30 minutes at the reflux temperature of toluene. After that, the system was cooled to 75° C. and 63 g (285.7 μmoL) 3-methacryloyloxypropyl dimethylchlorosilane was added dropwise. When the dropwise addition was over, the system was heated at 80° C. under agitation for 30 minutes. When a portion of the reaction mixture was analyzed using gas chromatography ("GLC" below), the peak of 3-methacryloyloxypropyl dimethylchlorosilane had disappeared. After that, a toluene solution of 3-methacryloyloxypropyl dimethylchlorosilane was obtained by filtering off the by-produced sodium chloride and unreacted sodium acetate.

Next, the entire amount of the toluene solution, 63.4 g (285.7 μmoL) hexamethylcyclotrisiloxane, and 0.17 g (1.15 μmoL) trifluoromethanesulfonic acid were placed in a separate flask furnished with an agitator and subjected to agitation for 1 hour at 30° C. and 1 hour at 50° C. When a portion of the reaction mixture was analyzed using GLC, it was found that about 23% of 3-methacryloyloxypropyldimethylacetyloxysilane had been converted to 1-acetyloxy-7-methacryloyloxypropyl-1,1,3,3,5,5,7,7-octamethyltetrasiloxane. After that, the system was neutralized by adding 2.9 g (28.3 μmoL) triethylamine. A toluene solution was obtained by removing the by-produced salt by decantation. 90.3 g of a liquid was obtained from this toluene solution by heating the low boiling point fraction at 80° C. under a reduced pressure of 1 mmHg for 30 minutes. 0.09 g 3,5-di-t-butyl-4-hydroxyphenylmethyldimethylammonium chloride, 0.006 g hydroquinone monomethyl ether, and 0.006 g 2,6-di-t-butyl-4-methylphenol were added to 60 g of the liquid and 10.1 g (corresponds to a yield of 11.2%) of the 136~142° C./1 mmHg fraction was obtained by distillation under reduced pressure. Analysis of the fraction using ¹H-NMR and IR showed that it consisted of 1-acetyloxy-7-(3-methacryloyloxypropyl)-1,1,3,3,5,5,7,7-octamethyltetrasiloxane represented by the following formula (9):

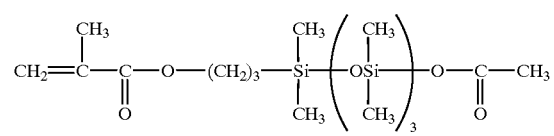

(9)

The purity of the siloxane as determined by GLC was 85.3%.

Thus it has been shown that the 1-acyloxy-organotetrasiloxane of the present invention is a novel compound and the production process of the present invention is characterized by the fact that it allows for efficiently preparing such novel siloxane.

What I claim is:

1. A 1-acyloxy-organotetrasiloxane comprising the general formula:

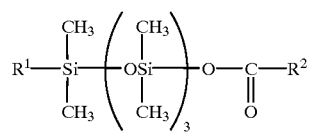

wherein $R^1$ is a monovalent organic group containing an acryloyloxy group or a monovalent organic group containing a methacryloyloxy group, and $R^2$ is a monovalent hydrocarbon group.

2. The 1-acyloxy-organotetrasiloxane according to claim 1, wherein $R^1$ is an acryloyloxyalkyl group or a methacryloyloxyalkyl group and $R^2$ is methyl.

3. The 1-acyloxy-organotetrasiloxane according to claim 2, wherein the methacryloyloxyalkyl group is 3-methacryloyloxypropyl.

4. A process for the production of a 1-acyloxy-organotetrasiloxane, comprising the step of (A) reacting hexamethylcyclotrisiloxane with an acyloxysilane in the presence of an acidic catalyst wherein the acyloxysilane has the general formula:

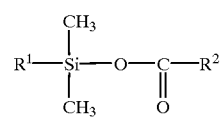

wherein $R^1$ is a monovalent organic group containing an acryloyloxy group or a monovalent organic group containing a methacryloyloxy group and $R^2$ is a monovalent hydrocarbon group.

5. The process according to claim 4, further comprising the steps of: (B) neutralizing the acidic catalyst with a base to produce a salt, (C) removing the salt, and (D) fractionally distilling the reaction mixture.

6. The process according to claim 4, wherein the step of reacting the hexamethylcyclotrisiloxane with the acyloxysilane is carried out in the presence of an organic solvent.

7. The process according to claim 4, wherein the acyloxysilane is present in at least an equimolar amount relative to the hexamethylcyclotrisiloxane.

8. The process according to claim 7, wherein the acyloxysilane is present in an amount ranging from 1 to 1.5 moles per mole of the hexamethylcyclotrisiloxane.

9. The process according to claim 4, wherein the acidic catalyst is selected from the group consisting of a protonic acid catalyst and a metal halide exhibiting Lewis acid properties.

10. The process according to claim 9, wherein the protonic acid catalyst is trifluoromethanesulfonic acid.

11. The process according to claims 9, wherein the acyloxysilane, hexamethylcylotrisiloxane, acidic catalyst, and optionally an organic solvent are mixed and reacted at room temperature.

12. The process according to claim 9, wherein the acyloxysilane, hexamethylcylotrisiloxane, acidic catalyst, and optionally an organic solvent are mixed and reacted under heating.

13. The process according to claim 9, wherein the metal halide is zinc chloride.

14. The process according to claim 4, wherein the acidic catalyst is a Friedel-Crafts acylation reaction catalyst consisting of a metal halide exhibiting Lewis acid properties and an acid halide.

15. The process according to claim 14, wherein the mole ratio of acid halide to metal halide is at least 1:1.

16. The process according to claims 14, wherein the acid halide contains an acyl group having the general formula:

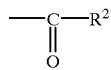

wherein $R^2$ is the same monovalent hydrocarbon group present in the acyloxysilane.

17. The process according to claim 14, wherein the acyloxysilane, hexamethylcylotrisiloxane, metal halide, acid halide, and optionally an organic solvent are mixed and reacted at room temperature.

18. The process according to claim 14, wherein the acyloxysilane, hexamethylcylotrisiloxane, metal halide, acid halide, and optionally an organic solvent are mixed and reacted under heating.

19. The process according to claims 17, wherein the metal halide and the acid halide are mixed and heated prior to mixing with the acyloxysilane, hexamethylcylotrisiloxane, and optional organic solvent.

20. The process according to claims 18, wherein the metal halide and the acid halide are mixed and heated prior to mixing with the acyloxysilane, hexamethylcylotrisiloxane, and optional organic solvent.

21. The process according to claim 4, wherein the acidic catalyst is a Friedel-Crafts acylation reaction catalyst consisting of a metal halide exhibiting Lewis acid properties and an acid anhydride.

22. The process according to claim 21, wherein the mole ratio of acid anhydride to metal halide is 0.5:1.

23. The process according to claim 21, wherein the mole ratio of acid anhydride to metal halide is at least 1:1.

24. The process according to claims 21, wherein the acid anhydride contains an acyl group having the general formula:

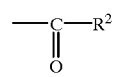

wherein $R^2$ is the same monovalent hydrocarbon group present in the acyloxysilane.

25. The process according to claim 21, wherein the acyloxysilane, hexamethylcylotrisiloxane, metal halide, acid anhydride, and optionally an organic solvent are mixed and reacted at room temperature.

26. The process according to claims 21, wherein the acyloxysilane, hexamethylcylotrisiloxane, metal halide, acid anhydride, and optionally an organic solvent are mixed and reacted under heating.

27. The process according to claim 25, wherein the metal halide and the acid anhydride are mixed and heated prior to mixing with acyloxysilane, hexamethylcylotrisiloxane, and optional organic solvent.

28. The process according to claims 26, wherein the metal halide and the acid anhydride are mixed and heated prior to mixing the acyloxysilane, hexamethylcylotrisiloxane, and optional organic solvent.

29. The product prepared according to the process of claim 4.

* * * * *